United States Patent [19]

Negita

[11] Patent Number: 5,125,273

[45] Date of Patent: Jun. 30, 1992

[54] METHOD AND APPARATUS FOR MEASURING THE SPEED OF AN ULTRASONIC WAVE

[75] Inventor: Keishi Negita, Kanagawa, Japan

[73] Assignee: Nissan Motor Company, Limited, Yokohama, Japan

[21] Appl. No.: 596,304

[22] Filed: Oct. 15, 1990

[30] Foreign Application Priority Data

Oct. 13, 1989 [JP] Japan .................................. 1-266421

[51] Int. Cl.$^5$ ............................................. G01N 29/18
[52] U.S. Cl. ......................................... 73/597; 73/602
[58] Field of Search ................. 73/589, 602, 597, 621, 73/627, 629, 645, 646; 367/902

[56] References Cited

U.S. PATENT DOCUMENTS

| | | | |
|---|---|---|---|
| 2,700,894 | 2/1955 | Van Valkenburg | 73/597 |
| 3,327,806 | 6/1967 | Anderson | 73/597 |
| 3,522,580 | 8/1970 | Lynch et al. | 73/597 |
| 4,079,315 | 3/1978 | Mohr | 73/597 |
| 4,095,457 | 6/1978 | Koda et al. | 73/597 |

FOREIGN PATENT DOCUMENTS

| | | |
|---|---|---|
| 1277065 | 6/1972 | United Kingdom . |
| 1332924 | 10/1973 | United Kingdom . |
| 1499884 | 9/1976 | United Kingdom . |

OTHER PUBLICATIONS

Papadakis, "Ultrasonic Phase Velocity by the Pulse-Echo-Overlap Method Incorporating Diffraction Phase Corrections", *The Journal of the Acoustical Society of America*, 40, 863–876 (1966).

McSkimin, "Pulse Superposition Method of Measuring Ultrasonic Wave Velocities in Solids", *The Journal of the Acoustical Society of America*, vol. 33, No. 1, Jan. 1966, pp. 12–16.

*Primary Examiner*—Hezron E. Williams
*Assistant Examiner*—Rose M. Finley
*Attorney, Agent, or Firm*—Foley & Lardner

[57] ABSTRACT

A method for measuring a propagation speed of ultrasonic wave transmission through a medium of known dimension, comprises a step of generating a plurality of pulse trains at each cycle of a predetermined time interval $t_i$, each of the RF pulse trains being composed of at least two consecutive RF pulses generated at a predetermined time period $t_s$ for exciting an output ultrasonic wave. The measuring method also includes the step of inputting a signal indicative of a superposed ultrasonic echo occurring due to the output ultrasonic wave applied to the medium, on a Y-axis of an oscilloscope, and inputting continuous X-axis trigger pulses having a predetermined period $t_o$ on an X-axis of the oscilloscope. The speed of the ultrasonic wave is derived on the basis of a length of the medium and the period $t_s$ read through the oscilloscope when an amplitude of the echo signal becomes greatest and the echo signals are overlapped in phase, by adjusting a value of the period $t_o$ while keeping the period relationship of $t_o = t_s = t_i/m$, wherein m is an integer which exceeds the number of the RF pulses of the RF pulse train.

10 Claims, 6 Drawing Sheets

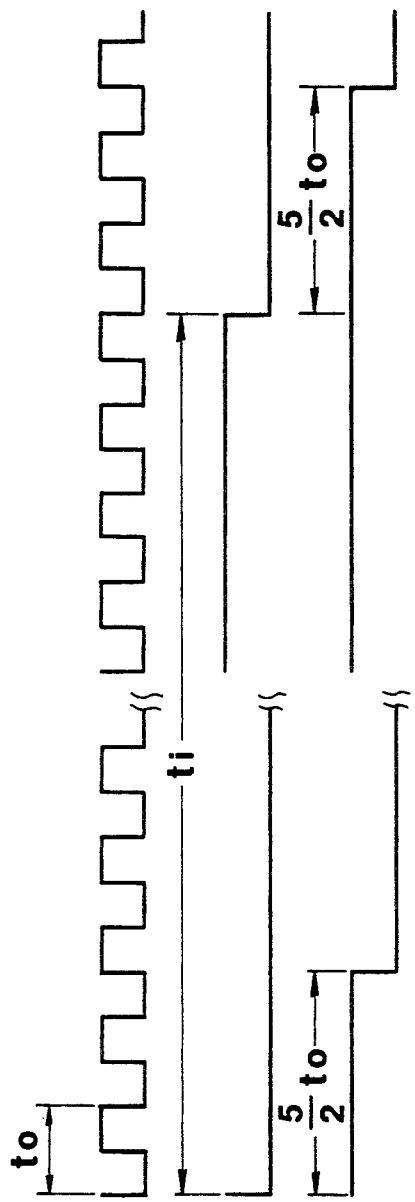
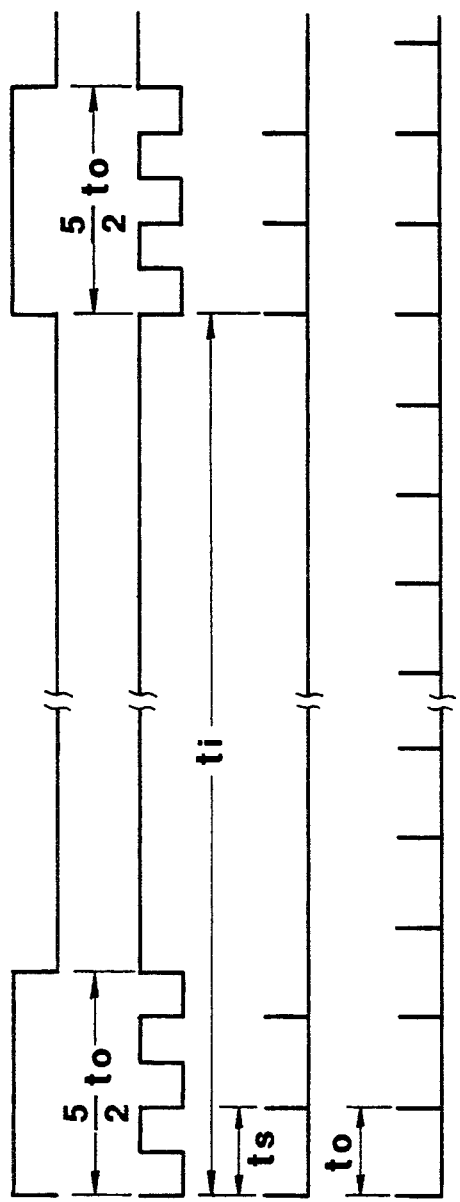
FIG.5a FIG.5b FIG.5c FIG.5d FIG.5e FIG.5f FIG.5g

FIG. 7(1-a)
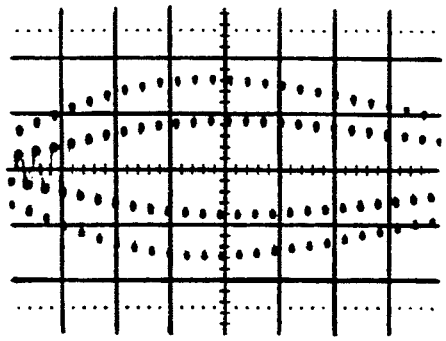
FIG. 7(1-b)
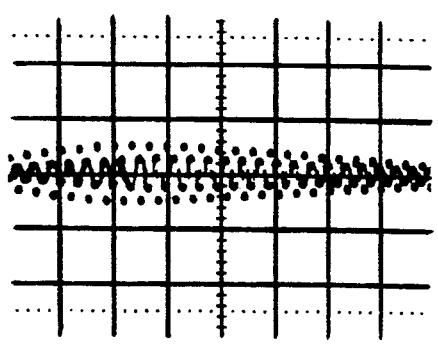
FIG. 7(2-a)
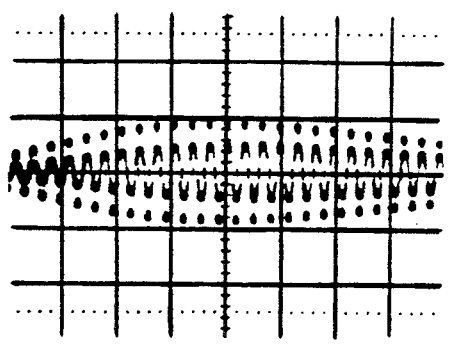
FIG. 7(2-b)
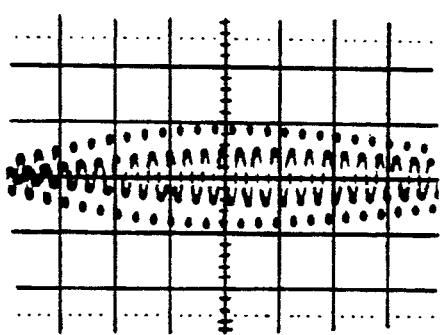
FIG. 7(3-a)
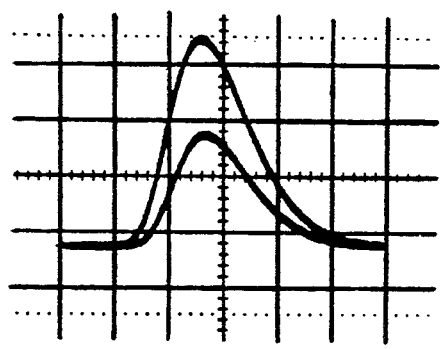
FIG. 7(3-b)
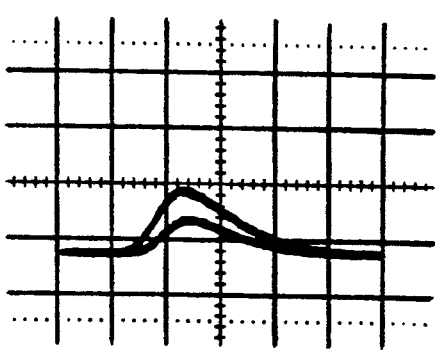

METHOD AND APPARATUS FOR MEASURING THE SPEED OF AN ULTRASONIC WAVE

BACKGROUND OF THE INVENTION

1. Field of the Invention

The present invention relates to an method and apparatus for measuring a propagation speed of a ultrasonic wave through various mediums such as liquids (for example, liquid ethanol) or solids. Specifically the invention relates to a method and apparatus for determining a ultrasonic propagation speed through an object, by observing a period of ultrasonic echo reflected from one end of the measured object, while applying an ultrasonic wave on the other end of the measured object.

2. Description of the Background Art

As is well known, there have been disclosed two conventional methods for measuring a propagation speed of ultrasonic wave transmission through various media. One such conventional ultrasonic speed measuring method is a "Pulse Echo Superposition Method", (herein abbreviated to "PES Method"), proposed by H. J. McSkimin. The PES Method has been detailed in "THE JOURNAL OF THE ACOUSTICAL SOCIETY OF AMERICA", Vol. 33, No. 1, 1961, pp12-16. The other conventional ultrasonic speed measuring method is a "Pulse Echo Overlap Method", (herein abbreviated to "PEO Method"), proposed by E. P. Papadakis et al. The PEO Method has been detailed in "THE JOURNAL OF THE ACOUSTICAL SOCIETY OF AMERICA", Vol. 42, No. 5, 1967, pp1045-1051.

In both the aforementioned conventional ultrasonic speed measuring methods, the propagation speed through a measured sample, having a predetermined dimension, can be obtained by deriving a calculated value $2X/t_r$ from a predetermined length X of the sample and a period $t_r$ of an ultrasonic echo reflected from one end of the sample, while applying an ultrasonic wave on the other end of the sample.

As shown in FIGS. 1A-1D, according to the PES Method, a plurality of exciting pulses for exciting ultrasonic waves are generated at a predetermined period of time $t_e$, as seen in FIG. 1A. As is generally known, the exciting pulses are formed with at least two radio-frequency pulses (herein abbreviated to "RF pulses"), each RF pulse having a predetermined pulse length $t_p$ and a predetermined frequency $f_{rf}$, i.e., a predetermined period $t_{rf}$. FIG. 1A shows an exemplified state wherein two RF pulses, namely a first RF pulse and a second RF pulse, are generated for exciting an output ultrasonic wave. In response to the exciting RF pulses, the output ultrasonic wave having the predetermined period of time $t_e$ is applied on one end of a measured sample through, for example, a piezoelectric transducer. Thereafter, the transducer receives a supersonic echo reflected from the other end of the sample and transduces sound pressure of the ultrasonic echo to an electric signal which will be referred to as an "ultrasonic echo signal". The ultrasonic echo signal can be observed on the screen of an oscilloscope. Note that, in the PES Method, a superposed echo, generated by superposition of ultrasonic echos occurring due to output ultrasonic waves excited by RF pulses is actually received by the transducer, since the exciting RF pulses are generated in close proximity to each other. For example, FIGS. 1B and 1C show an unsuperposed ultrasonic echo signal occurring via the first RF pulse and an unsuperposed ultrasonic echo signal occurring via the second RF pulse, respectively. On the other hand, FIG. 1D shows a superposed ultrasonic echo signal waveform actually observed on the screen of an oscilloscope, obtained by superposing the two echo signals shown in FIGS. 1B and 1C, under a condition wherein the predetermined period $t_e$ of the output ultrasonic wave (the exciting RF pulse) is consistent with a period of time $t_r$ of the ultrasonic echo or the ultrasonic echo signal. As seen in FIG. 1D, if the period of time $t_e$ of the exciting RF pulse is consistent with the period of time $t_r$ of the echo signal, the superposed ultrasonic echo signal provides the greatest amplitude by superposing the two echo signals. Therefore, a period of time $t_r$ of a ultrasonic echo signal can be obtained by monitoring a particular period of time $t_e$ of the RF pulse when the amplitude of the superposed ultrasonic echo signal, which is observed on an oscilloscope, becomes a maximum value. An ultrasonic speed of an ultrasonic wave traversing the measured sample can be calculated on the basis of a period $t_r$ of an ultrasonic echo signal, measured in accordance with the procedure as previously described.

However, as appreciated from FIGS. 1A-1D, in the aforementioned PES Method, the amplitude of the superposed ultrasonic echo signal may become greater, even if a period of time $t_e$ of the RF pulse is equal to a period of time $t_r \pm k \cdot t_{rf}$, wherein k is an integer, as well as a period of time $t_r$ of the echo signal. Therefore, to determine whether the period of time $t_e$ of the RF pulse is precisely consistent with the period of time $t_r$ of the ultrasonic echo signal, the condition of k=0 must be monitored and satisfied through visual observation on the screen of an oscilloscope. Although in FIGS. 1A-1D, the number of waves of the RF pulse or the ultrasonic echo signal is illustrated as being extremely small for the purpose of simplification of the disclosure of the present invention, the number of waves of the actually utilized RF pulse is relatively large, substantially 30 with regard to one RF pulse, as the actual RF pulse has a predetermined pulse length $t_p$ of 2 μs, a period $t_{rf}$ of 0.067 μs, a frequency $f_{rf}$ of 15 MHz, for example. Therefore, the determination of the condition of k=0 through visual observation on the screen is practically impossible.

For this reason, when an ultrasonic propagation speed through various media of a predetermined size is actually measured in accordance with the PES Method, the operator must perform a particular procedure wherein the period $t_{rf}$ of the RF pulse is slightly varied so as to precisely determine the condition of $t_e = t_r$, i.e., k=0. According to the particular procedure, the operator may judge that the condition of k=0 is satisfied if the amplitude time period of a superposed echo signal does not vary when the period $t_{rf}$ of the RF pulse is varied under a condition wherein the period $t_e$ of the exciting RF pulse is adjusted such that the amplitude of the superposed echo signal becomes greatest. The equation $t_e = t_r$ is satisfied regardless of various values of the period of $t_{rf}$ of the RF pulse when the condition of k=0 is satisfied, as appreciated from the equation $t_e = t_r \pm k \cdot t_{rf}$, wherein k is an integer. Such a procedure, including selecting adjustment of the period $t_{rf}$ as well as the period $t_e$, is troublesome and requires a high degree of skill. Both adjustments of the periods $t_e$ and $t_{rf}$ require a relatively long measuring time.

As shown in FIGS. 6A-6C, according to the PEO Method, an exciting pulse for exciting an ultrasonic wave is cyclically generated at a predetermined period of time $t_i$, as seen in FIG. 6B. Simultaneously, a X-axis trigger pulse for an oscilloscope is generated at a predetermined period of time $t_o$ (wherein $t_o = t_i/m$ and $m = 10$, 100, or 1000, for example), as seen in FIG. 6C. In response to the cyclically generated exciting pulses, an output ultrasonic wave with the predetermined period of time $t_i$ is applied on one end of a measured sample through a piezoelectric transducer and thereafter the transducer receives an ultrasonic echo reflected from the other end of the sample and generates an ultrasonic echo signal. The ultrasonic echo signal is input on the Y-axis of the oscilloscope, while the X-axis trigger pulse is input on the X-axis of the oscilloscope. When the period of time $t_o$ of the trigger pulse is consistent with a period of time $t_r$ of the ultrasonic echo signal, the cyclically input echo signals are overlapped on each other in a same phase on the screen of the oscilloscope, as is generally known. In this manner, a period of time $t_r$ of the echo signal can be obtained by monitoring the period $t_o$ of the trigger pulse when the echo signals lie in a same phase while varying the period $t_o$ for the trigger pulse. An ultrasonic speed of an ultrasonic wave traversing a measured sample can be calculated on the basis of a period $t_r$ of an ultrasonic echo signal, measured in accordance with the procedure as previously noted.

However, in the PEO Method, it is difficult to determine whether or not the input ultrasonic echo signals lie in a same phase through visual observation on the screen of the oscilloscope, because the number of waves of the actually received echo signal is relatively large although the wave number of the echo signal is relatively small for the purpose of simplification of the disclosure of the present invention. Therefore, in the PEO Method, a quick measurement of an ultrasonic speed is difficult. Moreover, it will be appreciated that determination of phase matching of ultrasonic echo signals according to the PEO Method is difficult to automatize, as compared with monitoring a maximum amplitude of a superposed ultrasonic echo signal according to the PES Method.

SUMMARY OF THE INVENTION

It is, therefore, in view of the above disadvantages, an object of the present invention to provide a method for measuring a propagation speed of an ultrasonic wave traversing a measured object, by observing a period of an ultrasonic echo reflected from the measured object, wherein the period of the echo can be precisely and quickly determined.

It is another object of the invention to provide a measuring method for a propagation speed of an ultrasonic wave traversing a measured object, which is capable of automatizing a precise measurement of a period of an ultrasonic echo reflected from the measured object.

In order to accomplish the aforementioned and other objects, a method for measuring a propagation speed of an ultrasonic wave traversing a measured sample, comprises the steps of, a) generating a pulse train at each cycle of a predetermined time interval $t_i$, each of the pulse trains being composed of at least two consecutive pulses, one of the pulses being generated at a time period $t_s$, the period $t_i$ of the pulse train being determined in a manner so as to satisfy a condition of $t_i = mt_s$, wherein m is an integer which exceeds the number of pulses of the pulse train b) generating exciting pulses for exciting an output ultrasonic wave, in synchronization with each pulse of each of the pulse trains, c) applying the output ultrasonic wave to one end of a medium having a predetermined dimension, d) receiving a superposed ultrasonic echo reflected from the end of the medium opposite that which receives the output ultrasonic wave, the superposed ultrasonic echo occurring by consecutive pulses of the pulse train, e) inputting a signal representative of the superposed ultrasonic echo on a Y-axis of an oscilloscope, and inputting continuous X-axis trigger pulses on a X-axis of the oscilloscope, the X-axis trigger pulses having a predetermined time period $t_o$ being determined in a manner so as to satisfy a condition of $t_s = t_o$, and f) adjusting a value of the period $t_o$ such that an amplitude of the superposed ultrasonic echo signal becomes greatest and the superposed ultrasonic echo signals are overlapped in phase, while keeping the period relationship of $t_o = t_s = t_i/m$. The measuring method of the invention may also include the additional step of g) calculating the propagation speed of ultrasonic wave transmission through the medium, on the basis of an expression $2X/t_r$, wherein X is the length of the medium and $t_r$ is a period of the superposed ultrasonic echo, corresponding to the adjusted period $t_o$ of the step f). In general, the step b) of generating exciting pulses may include generating radio-frequency pulses in synchronization with each pulse of each of the pulse trains. The step c) of applying the output ultrasonic wave and the step d) of receiving the superposed ultrasonic echo, may include converting the exciting pulse to a sound pressure and converting a sound pressure to the superposed ultrasonic echo signal, respectively. The step f) of adjusting a value of the period $t_o$ may also be performed through visual observation on the oscilloscope.

According to another aspect of the invention, an apparatus for measuring a propagation speed of ultrasonic wave transmission through a medium, comprises a pulse generator for generating a pulse train at each cycle of a predetermined time interval $t_i$, each of the pulse trains being composed of at least two consecutive pulses, one of the pulses being generated at a time period $t_s$, the interval $t_i$ of the pulse train being determined in a manner so as to satisfy a condition of $t_i = mt_s$, wherein m is an integer which exceeds the number of pulses of the pulse train, means for generating exciting pulses for exciting an output ultrasonic wave, in synchronization with each pulse of each of the pulse trains, means for transducing an electrical signal to a sound pressure in a manner so as to apply the output ultrasonic wave to one end of a medium having a predetermined dimension and for transducing a sound pressure to an electrical signal in a manner so as to receive a superposed ultrasonic echo of the output ultrasonic wave reflected from the other end of the medium and to generate a superposed ultrasonic echo signal in synchronization with the superposed ultrasonic echo, and an oscilloscope for inputting the superposed ultrasonic echo signal generated from the transducing means on a Y-axis thereof and for inputting continuous X-axis trigger pulses on a X-axis thereof so as to sweep the superposed ultrasonic echo signal in a X-axis direction in synchronization with the X-axis trigger pulses, the X-axis trigger pulses having a predetermined time period $t_o$ being determined in a manner so as to satisfy a condition of $t_s = t_o$. In this construction, the propagation speed of the ultrasonic wave traversing the medium is derived on the basis of a length X of the medium and the period $t_o$ read through the oscilloscope when an amplitude of the superposed ultrasonic echo signal becomes greatest and the superposed ultrasonic echo signals are overlapped in phase, by adjusting a value of the period $t_o$, while keeping the period relationship of $t_o=t_s=t_i/m$. The pulse generator may include a rectangular pulse generating circuit for continuously generating rectangular pulses at the period $t_o$, a frequency divider for demultiplying the continuous pulses from the rectangular pulse generating circuit, a pulse train generating circuit for processing the continuous pulses from the rectangular pulse generating circuit and the demultiplied pulses from the frequency divider and for generating the pulse trains at the interval $t_i$, and a differentiating circuit for differentiating each pulse of each of the pulse trains in a manner so as to pass only the trailing edge component of each pulse of each of the pulse trains. The pulse train generating circuit may comprise a shift register including a series of at least two flip-flops, each flip-flop generating pulses shifted down by a predetermined period of time $(n-\frac{1}{2})t_o$, wherein n is an integer corresponding to the order of a sequential arrangement of the flip-flops, a switch for selecting an output from the flip-flops, a first NOT circuit for generating negative pulses on the basis of the demultiplied pulses from the frequency divider, a second NOT circuit for generating negative pulses on the basis of the continuous pulses from the rectangular pulse generating circuit, an AND circuit for generating a logical multiply on the basis of the shifted-down pulses selected through the switch and the negative pulses from the first NOT circuit, and a NAND circuit for generating the pulse trains on the basis of the negative pulses from the second NOT circuit and the logical multiply from the AND circuit. The pulse generator may include a circuit for generating the X-axis trigger pulses input on the X-axis of the oscilloscope and a circuit for generating intensity modulation pulses for enhancing luminance with regard only to a predetermined signal input on the Y-axis of the oscilloscope.

BRIEF DESCRIPTION OF THE DRAWINGS

FIGS. 5a-5g are time charts illustrating various pulses created by the circuits shown in FIGS. 3 and 4.

FIGS. 7(1-a) and 7(1-b) are photographs showing the relationship between superposed RF echo signals in the same phase, actually observed on an oscilloscope according to the ultrasonic speed measuring method of the invention.

FIGS. 7(3-a) and 7(3-b) are photographs showing the relationship between superposed video echo signals of the same phase actually observed on an oscilloscope according to the ultrasonic speed measuring method of the invention.

FIGS. 7(2-a) and 7(2-b) are photographs showing the overlapping relationship between RF echo signals actually observed on an oscilloscope according to the conventional PEO Method.

DESCRIPTION OF THE PREFERRED EMBODIMENT

Figures 1A, 1B, 1C, 1D:
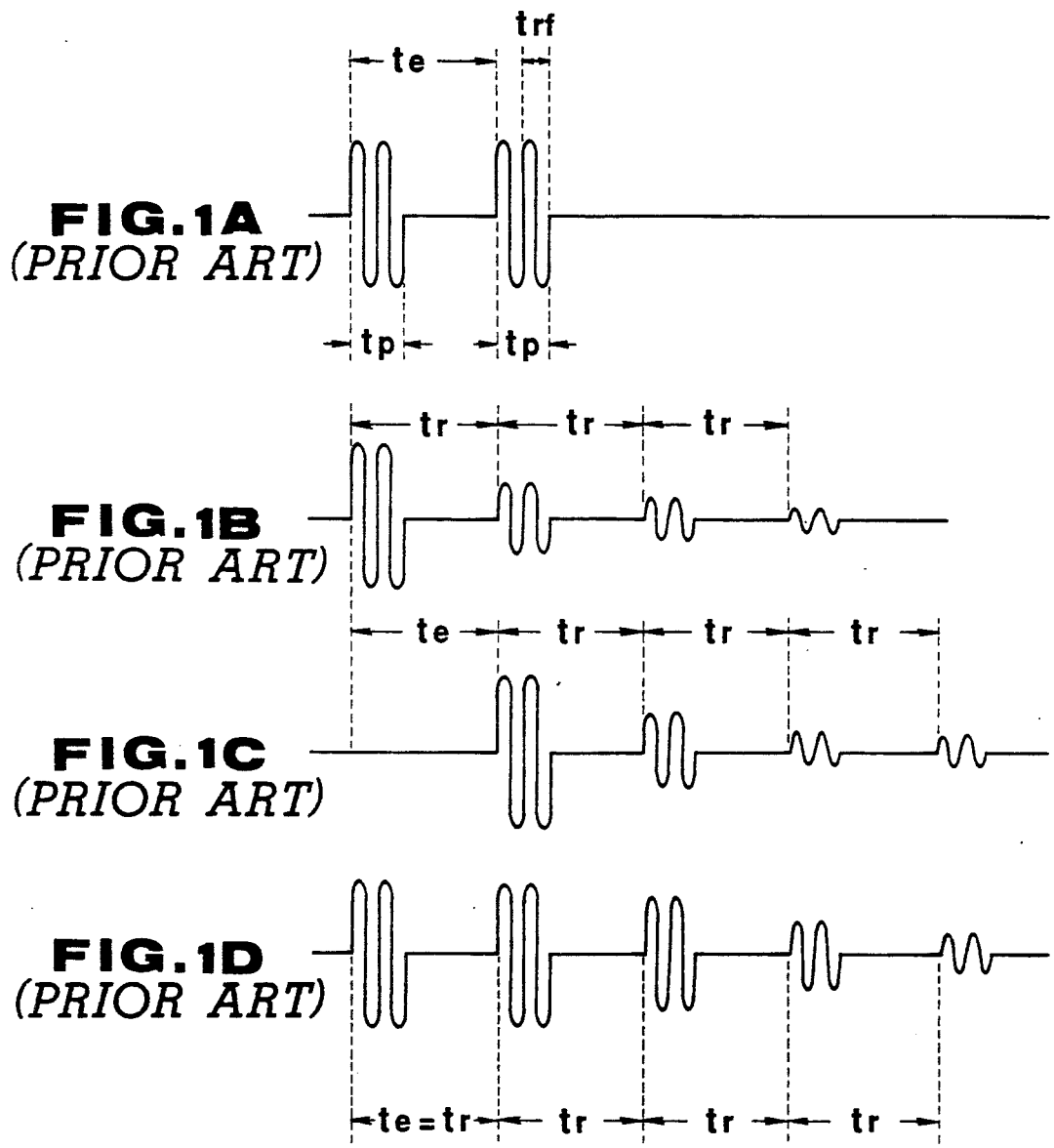
FIGS. 1A-1D are time charts illustrating various signals generated or received according to the conventional PES Method.
Figure 2:
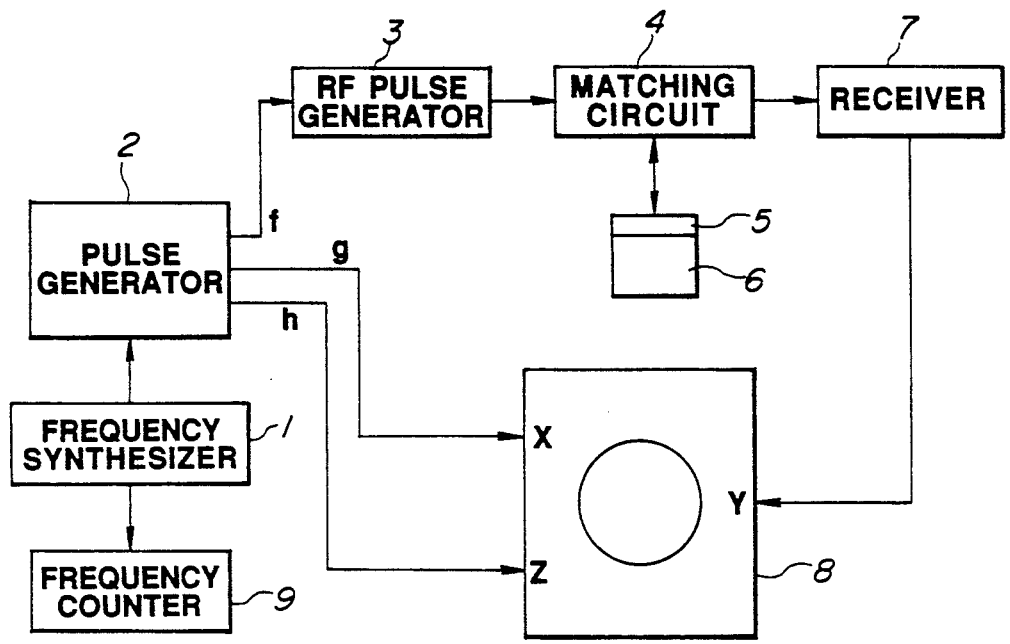
FIG. 2 is a block diagram illustrating a preferred embodiment of an apparatus for measuring ultrasonic propagation speed of ultrasonic wave transmission through various media, operable according to an ultrasonic speed measuring method of the invention.

Referring now to FIG. 2, a frequency synthesizer 1 operates as a standard signal generator, which generates a standard signal utilizing a time base in a manner so as to provide a high resolution of 0.1 ns. In general, a continuous wave, such as a sinusoidal wave is used as the standard signal created by the synthesizer 1. A frequency counter 9 is connected to the synthesizer 1 for counting the frequency of the standard signal output from the synthesizer 1 and for displaying its frequency. A pulse generator 2 is connected to the synthesizer 1, to convert the continuous wave to pulse trains required to measure an ultrasonic speed of wave being tranorsed through an object of known dimension. The pulse generator 2 generates three different pulses, namely a pulse f required to initiate an exciting pulse for exciting an output ultrasonic wave, as seen in FIGS. 5f and 6D, a X-axis trigger pulse g for an oscilloscope or a synchroscope 8, an intensity modulation pulse h for enhancing luminance with regard only to a predetermined echo signal. A RF pulse is generally utilized as the exciting pulse. The apparatus executing the ultrasonic speed measuring method of the invention also includes a RF pulse generator 3 being composed of a pulsed oscillator and a RF amplifier. The RF pulse generator 3 converts the pulses f from the pulse generator 2 to RF pulses and outputs an amplified RF pulses (as seen in FIG. 1A), each having 200 V (peak to peak), in synchronization with the pulses f. The RF pulse is equivalent to a pulse length of $t_p=1$ $\mu s - 2$ $\mu s$, and a frequency $f_{rf}=15$ MHz. A matching circuit 4 is also provided between the RF pulse generator 3 and a transducer 5 for the purpose of impedance matching between the RF amplifier having a low impedance, for example 50 ohm and a transducer 5 having a relatively high impedance. A piezo-electric transducer is conventionally used as the transducer 5. The transducer 5 synchronously applies an output ultrasonic wave to one end of a measured sample 6 in response to the amplified RF pulses from the RF pulse generator 3 and receives an ultrasonic echo reflected from the other end of the sample 6. Thereafter, the transducer 5 transduces sound pressure of the ultrasonic echo to an ultrasonic echo signal. For instance, various objects having a predetermined length of 10 mm and being in a liquid state or in a solid state, may be used as a sample 6. A receiver 7 is connected to the matching circuit 4 through which the ultrasonic echo signal is input. The receiver 7 operates in such a manner as to amplify the received echo signal and to output an amplified RF echo signal to the Y-axis on the oscilloscope 8 or in such a manner as to demodulate the echo signal and to output the demodulated echo signal as a video signal to the Y-axis of the oscilloscope 8. The matching circuit 4 may also be applied for impedance matching between the transducer 5 and the receiver 7. As seen in FIG. 2, the oscilloscope 8 receives the pulse g as a X-axis trigger pulse, the amplified RF echo signal (or the video signal) as a Y-axis input, and the pulse h as a Z-axis input. The structure of the pulse generator 2 is hereinafter described in detail in accordance with the block diagram of FIG. 3.

Figure 3:
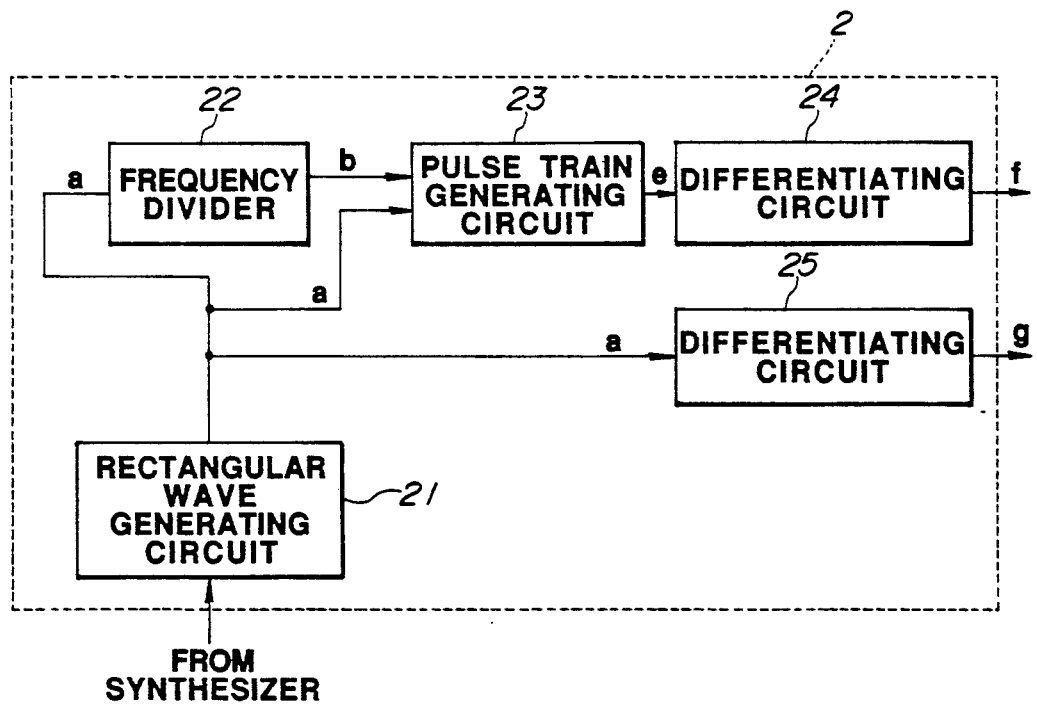
FIG. 3 is a block diagram illustrating one embodiment of a pulse generator included in the ultrasonic speed measuring apparatus shown in FIG. 2.

As shown in FIG. 3, the pulse generator 2 according to the embodiment is composed of a rectangular pulse generating circuit 21, a frequency divider 22, a pulse train generating circuit 23, and two differentiating circuits 24 and 25. The rectangular pulse generating circuit 21 continuously generates rectangular pulses a at a predetermined period of time $t_o$ as shown in FIG. 5a, on the basis of the standard signal from the synthesizer 1. The frequency divider 22 demultiplies the pulses a and generates demultiplied pulses b having a predetermined time interval $t_i$ as shown in FIG. 5b. The input terminal of the pulse train generating circuit 23 is connected to the output terminals of both the circuit 21 and the divider 22, to receive the pulses a and the pulses b, respectively. The circuit 23 processes the pulses a and b and generates pulse trains e at each cycle of the predetermined time interval $t_i$ as shown in FIG. 5e. The differentiating circuit 24 receives a plurality of pulse trains e from the pulse train circuit 23 and differentiates each pulse of the pulse trains e in a manner so as to pass only the trailing edge component of each pulse of the pulse trains e. Thereafter, the differentiating circuit 24 generates differentiated pulse trains f as shown in FIG. 5f. On the other hand, the input terminal of the differentiating circuit 25 is connected to the output terminal of the rectangular pulse generating circuit 21. The differentiating circuit 25 receives the pulses a from the circuit 21 and differentiates each pulse a in the same manner as the differentiating circuit 24 and continuously generates X-axis trigger pulses g at the predetermined period of time $t_o$ as seen in FIG. 5g. The previously noted pulse train generating circuit 23 and the differentiating circuit 24 are hereinbelow detailed in accordance with the block diagram of FIG. 4.

Figure 4:
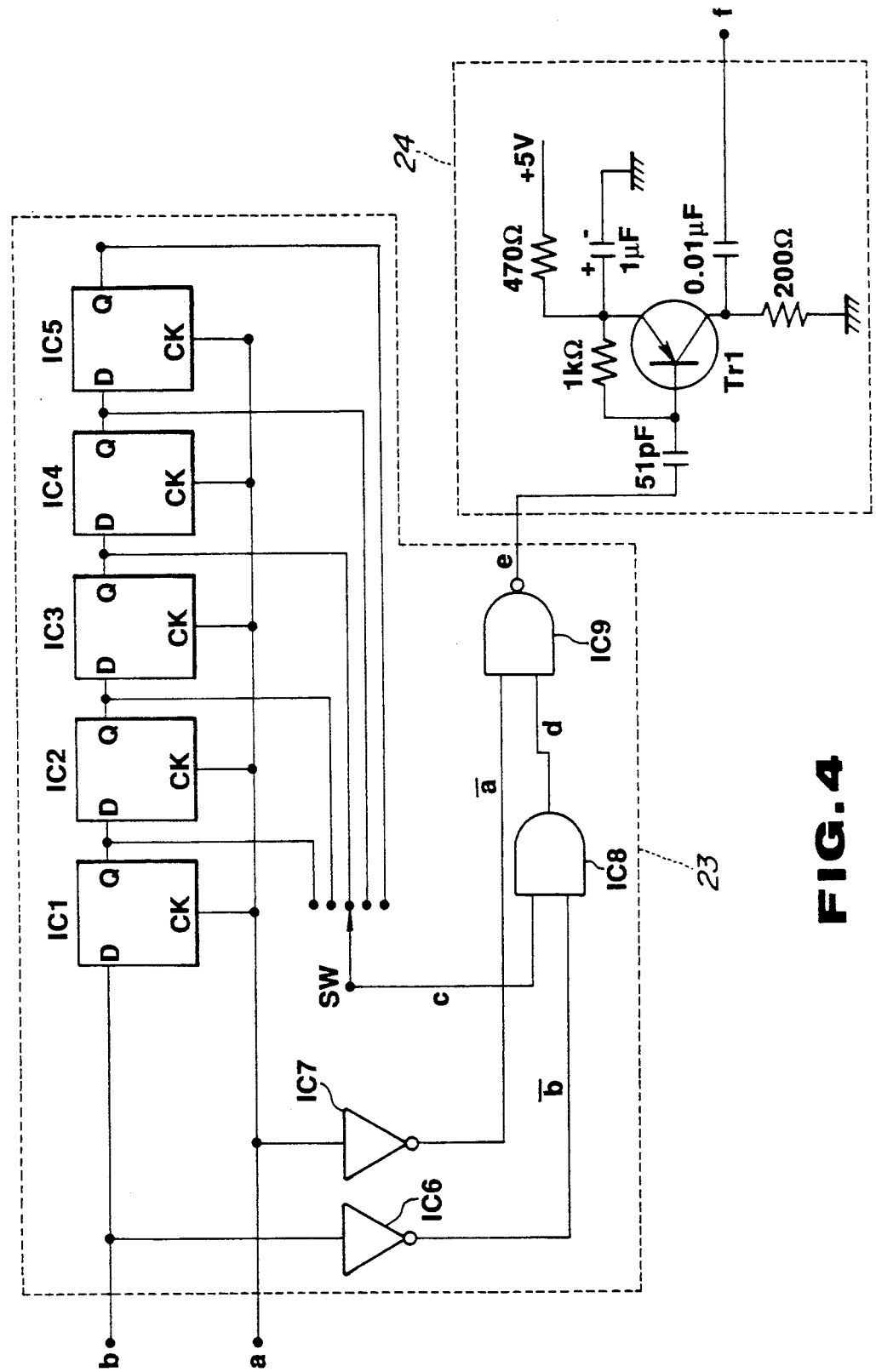
FIG. 4 is a circuit diagram illustrating one embodiment of a pulse-train generating circuit and a differentiating circuit included in the pulse generator shown in FIG. 3.

Referring now to FIG. 4, the pulse train generating circuit 23 is composed of a shift register including a series of flip-flops IC1-IC5, two NOT circuits IC6 and IC7, an AND circuit IC8, a NAND circuit IC9, and a switching unit SW. As clearly seen in FIG. 4, the D terminal of a first flip-flop IC1 receives the pulses b from the divider 22, while the CK terminal of the flip-flop IC1 receives the continuous pulses a from the rectangular pulse generating circuit 21. The pulses a serve as clock pulses for each flip-flop. The flip-flops IC1-IC5 respectively generate the pulses c shifted down by a predetermined period of time $\frac{1}{2}t_o$, $3/2t_o$, $5/2t_o$, $7/2t_o$, and $9/2t_o$, through each Q terminal thereof. The shifted-down pulses c are selectively output through the switch SW into one of the input terminals of the AND circuit IC8. In the embodiment, the shifted-down pulses c may be output from the Q terminal of the flip-flop IC3 through the switch SW into the AND circuit IC8, for example. The output pulses c from the flip-flop IC3 are seen in FIG. 5c. On the other hand, the other input terminal of the AND circuit IC8 receives pulses $\overline{b}$ (negative b) through the NOT circuit IC6 whose input terminal receives the pulses b from the divider 22. Thus, the AND circuit IC8 outputs the pulses d (corresponding to c.$\overline{b}$) as shown in FIG. 5d. Furthermore, the NAND circuit IC9 receives pulses $\overline{a}$ (negative a) gained through the NOT circuit IC7 and the pulses d and thus generates the pulses e (corresponding to $(a+\overline{d})$) as shown in FIG. 5e.

In FIG. 4, the differentiating circuit 24 is composed of a transistor $T_{r1}$, a plurality of condensers, and plural resistances. The differentiating circuit 24 converts the rectangular pulse trains e to a group of differentiated pulse trains f as shown in FIG. 5f. The number of pulses constructing each pulse train f may be selected by the switch SW associated with the Q terminal of each flip-flop. In the embodiment, the switch SW selects the output of the flip-flop IC3 with the result that the pulse number of one pulse train f is set to "3". Although, in the embodiment, the pulse number can be selected from 1, 2, 3, 4 or 5, the pulse number may be properly varied, depending upon the number of the flip-flops included in the shift register. For example, if an additional flip-flop is connected to the fifth flip-flop IC5, a selectable pulse number of the pulse train f may be increased to a value of "6".

The ultrasonic speed measuring method of the invention, utilizing the measuring system shown in FIG. 2 is hereinbelow detailed in accordance with the time charts of FIG. 6.

Figure 6A:
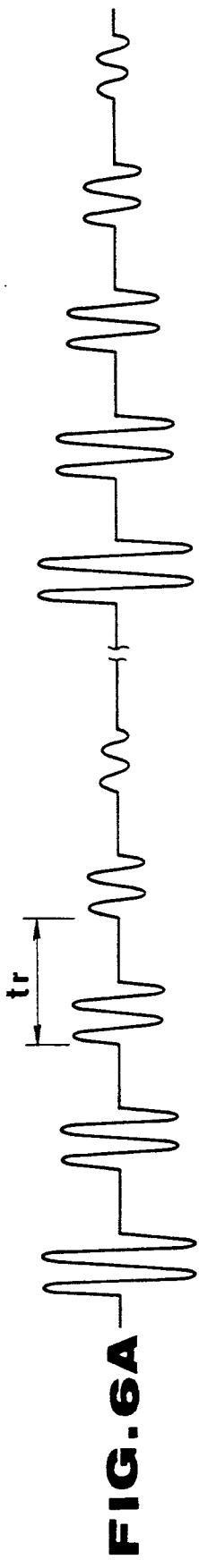
FIGS. 6A-6D are time charts illustrating various pulses created by the pulse generator shown in FIG. 3 and an ultrasonic echo signal input on the Y-axis of an oscilloscope, according to the ultrasonic speed measuring method of the invention.
Figure 6B:
Figure 6C:
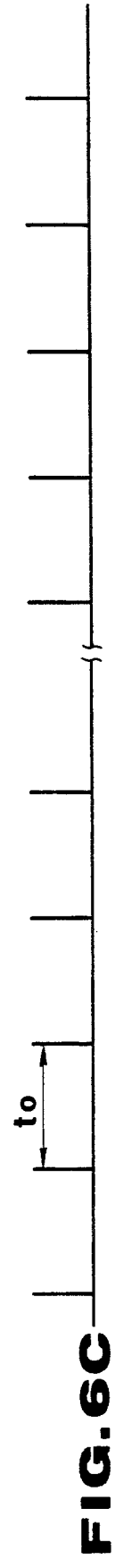
Figure 6D:
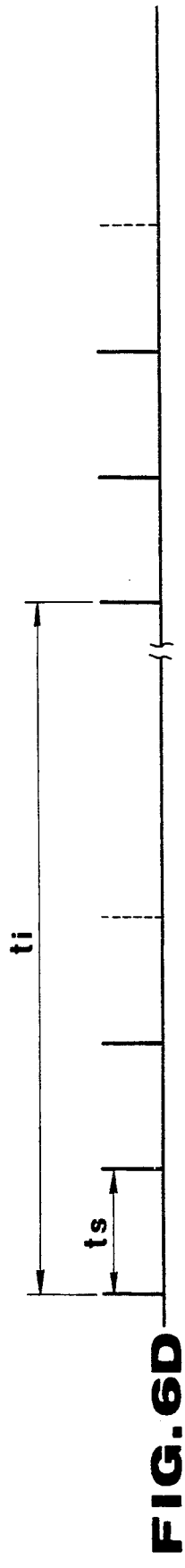

Referring now to FIGS. 6A–6D, the pulse generator 2 cyclically generates a plurality of pulse trains f as clearly seen in FIG. 6D (corresponding to the pulse trains seen in FIG. 5f) at a predetermined time interval $t_i$. One of the pulse trains f is formed with at least two differentiated pulses having a predetermined period $t_s$. Note that the time interval $t_i$ is preset in such a manner as to satisfy the expression ($t_i = mt_s$, m > n wherein m and n are integers respectively, and n is 2 or more). The integer n corresponds to the number of the pulses constructing one pulse train f. The period $t_i$ may be selected within a range of $10t_s$ to $1000t_s$, for example. The pulse generator 2 simultaneously generates X-axis trigger pulses g for the oscilloscope 8 at a predetermined period $t_o$ as seen in FIG. 6C. Note that the period $t_o$ of the X-axis trigger pulses g is preset in such a manner as to be equal to the period $t_s$ of the pulses included in the exciting pulse train f. The transducer 5 is driven by the multiplied RF pulses (as seen in FIG. 1A) generated by the RF pulse generator 3 in synchronization with the pulses f and applies an output ultrasonic wave on the sample 6. Thereafter the transducer 5 receives an ultrasonic echo from the sample 6 and generates ultrasonic echo signals. It will be appreciated that the ultrasonic measuring method according to the invention is different from the conventional PEO Method in that, in the measuring method of the invention, an exciting pulse train formed with at least two continuous RF pulses is applied to the transducer 5 at each cycle of a predetermined time interval $t_i$. Therefore, at least two continuous echo signals, occurring due to the at least two continuous RF pulses, are superposed and input on the Y-axis of the oscilloscope 8. In addition, the superposed echo signals are cyclically input on the Y-axis of the oscilloscope 8, and swept on the X-axis of the oscilloscope 8 in synchronization with the period $t_o$ of the X-axis trigger pulses. Thus, the superposed echo signals are overlapped on the screen of the oscilloscope 8. If the period $t_o (= t_s)$ of the trigger pulse is equal to the period $t_r$ of the superposed echo signal, the superposed echo signals lie in the same phase on the screen and in addition each amplitude of the superposed echo signals becomes greatest as seen in FIG. 7(1-a). In this manner, a period of time $t_r$ of the superposed echo signal can be obtained by monitoring the period $t_o$ of the trigger pulse when the superposed echo signals lie in phase and each amplitude of the superposed echo signals becomes greatest, varying the period $t_o$, while the condition of $(t_o=t_s=t_i/m, m>n$, wherein m and n are integers and n is equal to or greater than 2) is kept. As appreciated from the detailed description of circuits shown in FIGS. 2, 3 and 4, the aforementioned condition of $(t_o=t_s=t_i/m)$ can be automatically kept. In this manner, an ultrasonic speed of ultrasonic wave transmission can be calculated on the basis of a period $t_r$ of a superposed ultrasonic echo signal, measured in accordance with the procedure as previously noted.

Referring now to FIGS. 7(1-a), 7(1-b), 7(2-a), 7(2-b), 7(3-a) and 7(3-b), these photographs are actual oscilloscope observations by the inventor of the present invention. These test data are observed under a condition wherein liquid ethanol is utilized as a sample and an exciting RF pulse having a predetermined pulse length of 2 μs, a predetermined frequency of 15 MHz (a predetermined period of 0.067 μs); was used as an exciting pulse for the output ultrasonic wave applied to the sample. In FIGS. 7(1-a), 7(1-b), 7(2-a) and 7(2-b), one division corresponds to 0.2 μs in a X-axis direction of the oscilloscope, while in FIGS. 7(3-a) and 7(3-b), one division corresponds to 1 μs in a X-axis direction of the oscilloscope.

As appreciated from FIGS. 7(1-a) or 7(3-a), when a period $t_o$ of a X-axis trigger pulse is consistent with a period $t_r$ of a superposed echo signal, the superposed echo signals are overlapped in phase and the amplitudes of each signal are relatively great. On the other hand, when the period $t_o$ is not consistent with the period $t_r$ as seen in FIGS. 7(1-b) and 7(3-b), the superposed echo signals do not lie in a same phase and the amplitude of each superposed echo signals is relatively small.

As previously described, a quick measurement of a precise period $t_r$ of a superposed echo signal can be accomplished by varying only a period $t_o$ of a X-axis trigger pulse in such a manner as to satisfy both phase matching and the greatest amplitude with regard to superposed echo signals. According to an ultrasonic speed measuring method of the invention, a period $t_o$ of a X-axis trigger pulse, a period $t_s$ of pulses constructing an exciting pulse train, and a time interval $t_i$ for generating a group of pulse trains are automatically preset in such a manner as to keep a particular condition of $t_o=t_s=t_i/m$, $m>n$, wherein m and n are integers and n is 2 or more, by varying one parameter $t_o$. Furthermore, monitoring the greatest amplitude of a superposed echo signal is an easy process to automate. Therefore, the measuring method according to the invention, for measuring ultrasonic transmission through a sample of known dimension, particularly a period of a superposed ultrasonic echo reflected from the sample, may be easily automated. The speed of the ultrasonic wave being transmitted through the sample may be monitored under various environmental conditions, for example various temperatures, while measuring. If a precise period of the superposed ultrasonic echo reflected from the sample is obtained on the basis of the previously noted two conditions according to the invention at a certain atmospheric temperature, various periods of the superposed ultrasonic echo, measured at other temperatures, can be quickly and precisely obtained by only the adjustment of the period $t_o$ of the X-axis trigger pulse for an oscilloscope. As set forth above, the period $t_r$ of the superposed echo signal is derived by monitoring the period $t_o$ precisely adjusted in accordance with the procedure as previously noted. Thereafter the adjusted period $t_o$ may be entered in a calculator and a required propagation speed of ultrasonic wave transmission through the sample having a predetermined length may be easily calculated on the basis of the expression $2l/t_r$.

Conversely, as appreciated from FIGS. 7(2-a) and 7(2-b), in the conventional PEO Method, since the amplitude of an unsuperposed echo signal is constant regardless of phase-matching and phase-unmatching of the echo signals, a precise determination of phase matching of the echo signals through visual observation on the screen requires extreme skill and may require a relatively long time for measurement.

While the foregoing is a description of the preferred embodiment for carrying out the invention, it will be understood that the invention is not limited to the particular embodiment shown and described herein, but may include variations and modifications without departing from the scope or spirit of this invention as described by the following claims.

What is claimed is:

1. A method for measuring a propagation speed of ultrasonic wave transmission through a medium, comprising the steps of:
   a) generating a pulse train at each cycle of a predetermined time interval $t_i$, each pulse train being composed of at least two consecutive pulses, one of said pulses being generated at a time period $t_s$, said interval $t_i$ of said pulse train being set in a manner so as to satisfy a condition of $t_i=mt_s$, wherein m is an integer which exceeds the number of pulses of said pulse train;
   b) generating an exciting pulse for exciting an output ultrasonic wave, in synchronization with each pulse of said pulse train;
   c) applying said output ultrasonic wave to one end of said medium having an ascertainable dimension;
   d) receiving a superposed ultrasonic echo reflected from an end of said medium opposite that which receives said output ultrasonic wave, said superposed ultrasonic echo generated by superposition of ultrasonic echos which are reflected and occur due to said output ultrasonic wave generated in synchronization with each pulse of said pulse train;
   e) inputting a signal representative of said superposed ultrasonic echo on a Y-axis of an oscilloscope, and inputting continuous X-axis trigger pulses on an X-axis of said oscilloscope, said X-axis trigger pulses having a predetermined time period $t_o$ being set in a manner so as to satisfy a condition of $t_s=t_o$;
   f) adjusting a value of said period $t_o$ such that an amplitude of said superposed ultrasonic echo signal becomes greatest and superposed ultrasonic echo signals are overlapped in phase, while maintaining a period relationship of $t_o=t_s=t_i/m$; and
   g) deriving said propagation speed of ultrasonic wave transmission through said medium on the basis of a length l of a sample and said period $t_o$ adjusted in accordance with step f).

2. The method as set forth in claim 1, comprising the additional step of:
   calculating said propagation speed of ultrasonic wave transmission through said medium, on the basis of an expression $2l/t_r$, wherein $t_r$ is a period of superposed ultrasonic echo, corresponding to adjusted period $t_o$ of step f).

3. The method as set forth in claim 1, wherein step b) of generating an exciting pulse includes generating a radio-frequency pulse in synchronization with each pulse of said pulse train.

4. The method as set forth in claim 1, wherein step c) of applying said output ultrasonic wave and step d) of receiving said superposed ultrasonic echo include converting an exciting pulse to a sound pressure and converting a sound pressure to said superposed ultrasonic echo signal, respectively.

5. The method as set forth in claim 1, wherein step f) of adjusting a value of said period $t_o$ is performed through visual observation on said oscilloscope.

6. An apparatus for measuring a propagation speed of ultrasonic wave transmission through a medium, said apparatus comprising:
- a pulse generator generating a pulse train at each cycle of a predetermined time interval $t_i$, each pulse train being composed of at least two consecutive pulses, one of said pulses being generated at a time period $t_s$, said pulse generator generating continuous X-axis trigger pulses having a predetermined time period $t_o$, said pulse generator maintaining a period relationship $t_o = t_s = t_i/m$, wherein m is an integer which exceeds the number of pulses of said pulse train;
- a first circuit generating an exciting pulse for exciting an output ultrasonic wave, in synchronization with each pulse of said pulse train;
- a second circuit transducing an electrical signal to a sound pressure to apply said output ultrasonic wave to one end of said medium having an ascertainable dimension and transducing a sound pressure to an electrical signal to receive a superposed ultrasonic echo generated by superposition of ultrasonic echos which are reflected from another end of said medium and occur due to said output ultrasonic wave generated in synchronization with each pulse of said pulse train, and to generate a superposed ultrasonic echo signal in synchronization with said superposed ultrasonic echo; and
- an oscilloscope inputting said superposed ultrasonic echo signal generated from said second circuit on a Y-axis of said oscilloscope and inputting said continuous X-axis trigger pulses on a X-axis of said oscilloscope to sweep said superposed ultrasonic echo signal in a X-axis direction in synchronization with said X-axis trigger pulses.

7. The apparatus as set forth in claim 6, wherein said pulse generator includes a rectangular pulse generating circuit continuously generating rectangular pulses at said period $t_o$, a frequency divider demultiplying continuous pulses from said rectangular pulse generating circuit, a pulse train generating circuit processing said continuous pulses from said rectangular pulse generating circuit and demultiplied pulses from said frequency divider and generating said pulse train at said interval $t_i$, and a differentiating circuit differentiating each pulse of said pulse train in a manner so as to pass only a trailing edge component of each pulse of said pulse train.

8. The apparatus as set forth in claim 7, wherein said pulse train generating circuit comprises a shift register which includes a series of at least two flip-flops, each flip-flop generating pulses shifted down by a predetermined period of time $(n - \frac{1}{2}) t_o$, wherein n is an integer corresponding to an order of a sequential arrangement of said flip-flops, a switch selecting an output from said flip-flops, a first NOT circuit generating negative pulses on the basis of said demultiplied pulses from said frequency divider, a second NOT circuit generating negative pulses on the basis of continuous pulses from said rectangular pulse generating circuit, an AND circuit generating a logical multiply on the basis of shifted-down pulses selected through said switch and negative pulses from said first NOT circuit, and a NAND circuit generating said pulse trains on the basis of negative pulses from said second NOT circuit and a logical product from said AND circuit.

9. The apparatus as set forth in claim 7, wherein said pulse generator includes a circuit generating intensity modulation pulses for enhancing luminance with regard only to a predetermined signal input on said Y-axis of said oscilloscope.

10. The apparatus as set forth in claim 6, further comprising means for deriving said propagation speed of said ultrasonic wave traversing said medium, on the basis of a length l of said medium and said period $t_o$ read from said oscilloscope when an amplitude of said superposed ultrasonic echo signal becomes greatest and superposed ultrasonic echo signals are overlapped in phase, by adjusting a value of said period $t_o$.

* * * * *